United States Patent
Berguer (12)

(10) Patent No.: US 6,183,438 B1
(45) Date of Patent: Feb. 6, 2001

(54) CATHETER WITH CENTERING WIRE

(76) Inventor: Ramon Berguer, 5755 Bloomfield Glens, West Bloomfield, MI (US) 48322

( * ) Notice: Under 35 U.S.C. 154(b), the term of this patent shall be extended for 0 days.

(21) Appl. No.: 09/477,316

(22) Filed: Jan. 4, 2000

(51) Int. Cl.$^7$ .................................................. A61M 29/00
(52) U.S. Cl. .......................................... 604/107; 604/104
(58) Field of Search .................. 600/585; 606/191–194; 604/264, 96.01, 101.1, 104–109

(56) References Cited

U.S. PATENT DOCUMENTS

| 4,928,693 | * | 5/1990 | Goodin et al. | 128/637 |
| 4,935,008 | * | 6/1990 | Lewis, Jr. | 604/52 |
| 4,994,069 | * | 2/1991 | Ritchart et al. | 606/191 |
| 5,315,747 | * | 5/1994 | Solar | 29/447 |
| 6,019,737 | * | 2/2000 | Murata | 600/585 |

* cited by examiner

*Primary Examiner*—Manuel Mendez
(74) *Attorney, Agent, or Firm*—Reising, Ethington, Barnes, Kisselle, Learman & McCulloch, PC

(57) ABSTRACT

An intravascular catheter has an outer end portion formed with a discharge orifice. A flexible centering wire supports the outer end portion of the catheter within a blood vessel while a treating agent is delivered into the blood vessel through the discharge orifice. The centering wire, in its natural, free state condition, has a coiled distal end portion. The centering wire is received lengthwise within a channel in the catheter. The centering wire is slidable in the channel from a retracted position to an operative position in which the distal end portion of the wire projects outwardly from the channel through a channel outlet and assumes its natural, coiled condition in contact with the interior wall of the blood vessel to support the outer end portion of the catheter within the blood vessel. The outer end portion of the catheter is centered within the blood vessel, out of contact with the interior wall of the blood vessel.

8 Claims, 1 Drawing Sheet

CATHETER WITH CENTERING WIRE

FIELD OF INVENTION

This invention relates generally to intravascular catheters and more particularly to a centering wire for supporting the distal end portion of a catheter within a blood vessel at or near the center or axis of flow within the vessel.

BACKGROUND AND SUMMARY

The present invention is particularly useful in catheters that remain in place within a blood vessel for an extended period of time, such as weeks or months. Such catheters are left in place to nourish patients who cannot be fed by mouth, or, more frequently, to administer chemotherapeutic drugs to treat cancer.

A catheter left on its own within a blood vessel tends to rest its tip against the vessel wall. This causes mechanical irritation of the vessel wall. In addition, the delivery of chemotherapeutic and other drugs against the vessel wall often causes inflammation and eventual thrombosis (clot formation) in the blood vessel. If the catheter tip is close to or in contact with the wall of the blood vessel where the flow is much slower, the undiluted chemicals delivered against the frail endothelial lining of the blood vessel will irritate it and set up local inflammation and thrombosis.

Conversely, if the catheter tip is at the center of the blood vessel, it is positioned at the axis of flow where flow is faster and chemicals delivered by the catheter tip are better mixed with blood and carried away from the wall faster. The chemical agents are also delivered at the greatest distance possible from the walls, that is, at the center of the blood vessel.

What is proposed by this invention is to maintain the catheter on the axis or center of flow in the blood vessel by use of a centering wire. Preferably, the centering wire is a flexible member having in its natural, free state condition a coiled, pigtail-like distal end portion. The centering wire is longitudinally slidable in a channel to an operative position in which the distal end portion projects from a channel outlet and assumes its natural, coiled condition in contact with the interior wall of the blood vessel. Preferably the coil at the distal end extends in an arc of 3600. The coil is sufficiently flexible to expand and contract as needed, depending on the inside diameter of the blood vessel.

One object of this invention is to provide a centering wire for supporting an intravascular catheter in a blood vessel having the foregoing features and capabilities.

Another object is to provide a centering wire for supporting an intravascular catheter within a blood vessel which is durable and long lasting in use, and is capable of being inexpensively manufactured and easily manipulated.

These and other objects, features and advantages of the invention will become more apparent as the following description proceeds, especially when considered with the accompanying claims and drawings.

DETAILED DESCRIPTION OF THE PREFERRED EMBODIMENT

Figure 2:
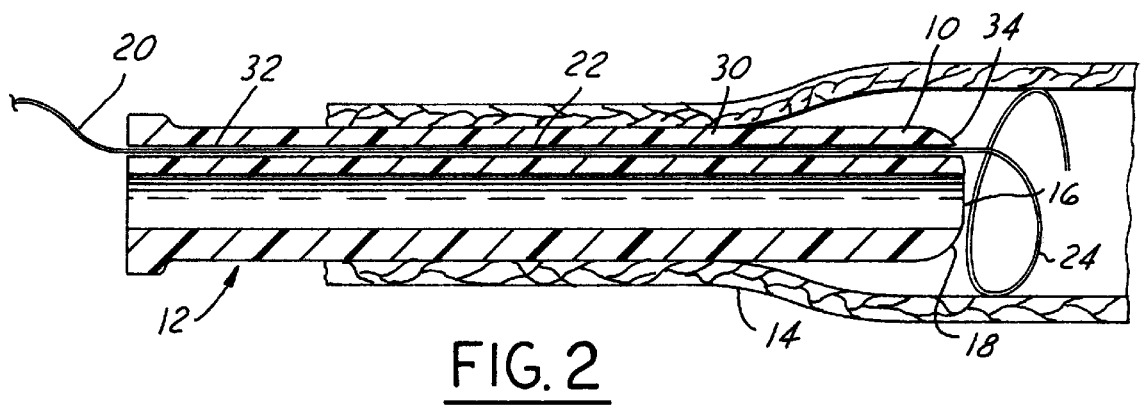
FIG. 2 is a view similar to FIG. 1, but shows the centering wire extended, with the distal end portion of the wire free to assume its coiled or pigtail shape, centering the outlet end portion of the catheter within a blood vessel.
Figure 3:
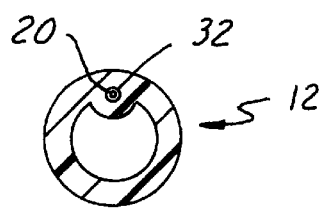
FIG. 3 is a sectional view of the catheter taken on the line 3—3 in FIG. 1.
Figure 4:
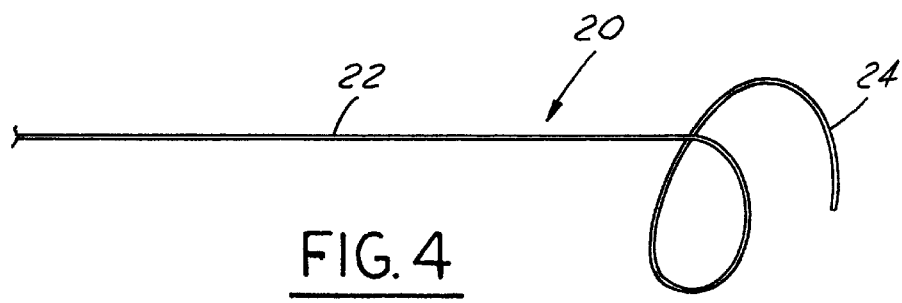
FIG. 4 is an elevational view of the centering wire in its natural, free state condition.

Referring now more particularly to the drawings, the distal or outer end portion 10 of a catheter 12 is shown supported within a blood vessel 14 of a patient (FIG. 2). The catheter 12 has an elongated flexible tubular body provided with a central orifice 16 at the tip 18 for the discharge of a flowable substance into the blood stream. The flowable substance may be any treating agent such as a chemotherapeutic drug or simple nourishment.

The outer end portion 10 of the catheter 12 is supported in the blood vessel by a centering wire 20. The centering wire 20 is a thin (about 0.035 inch in cross-section), elongated, flexible, resilient, spring-like member which may be made of spring steel or a suitable resinous thermoplastic material. A suitable thermoplastic is nitinol, which is a thermoplastic alloy.

The centering wire 20 has a main body portion 22 which is substantially straight, and a distal end portion 24 which is preshaped or coiled into the shape of a helix or pigtail. The helix of the distal end portion is preferably at least about 360° or more in extent and formed about the longitudinal axis of the main body portion 22.

A side wall 30 of the catheter 12 has an elongated channel 32 which extends lengthwise of the catheter and has a channel outlet 34 at the tip 18 but laterally offset from the orifice 16. The channel 32 defines a substantially straight passage for the centering wire. The centering wire 20 extends lengthwise within the channel 32, and, although closely confined, is longitudinally slidable within the channel from a retracted position shown in FIG. 1 to and extended, operative position shown in FIG. 2.

In the retracted position, the distal end portion 24 is wholly within the channel and is held straight by the channel. However, when extended, the distal end portion is projected outside the catheter and springs to its natural free state condition shown in FIG. 2 recovering its natural coiled or pigtail shape. Since the distal end portion is coiled about the longitudinal axis of the main body portion of the wire 20, and since the main body portion is confined within the channel 32, it is apparent that the distal end portion when in the extended operative position will have its axis generally parallel to the axis of the catheter and to the blood vessel and will spring out to the extent necessary to contact the interior wall of the blood vessel. If the centering wire is made of a thermoplastic material, contact with the warm blood of the patient will hasten the recovery of the distal end portion of the wire to its pigtail shape. Although flexible and compressible, the coiled distal end portion of the wire will maintain the outer end portion 10 of the catheter centered with respect to the blood vessel, yet out of contact with the interior wall of the blood vessel.

Figure 1:
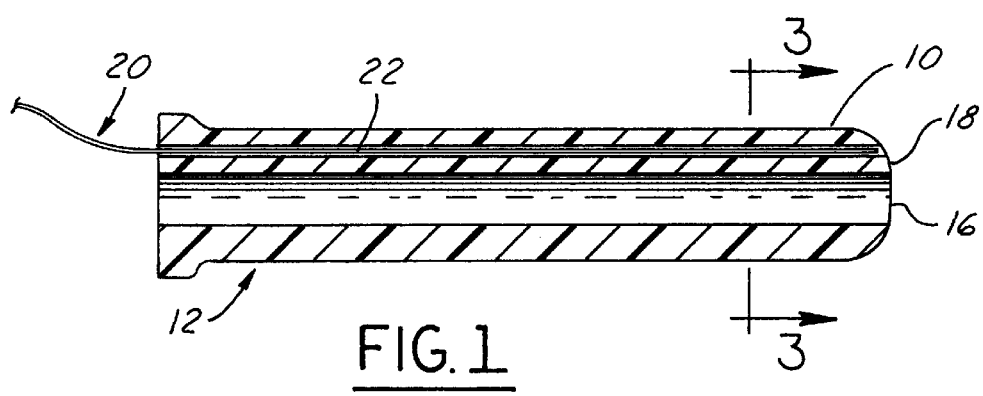
FIG. 1 is a fragmentary longitudinal sectional view showing a catheter and a centering wire retracted within a wire channel in the catheter, in accordance with the invention.

Prior to withdrawing the catheter from the blood vessel, the centering wire is retracted to the position shown in FIG. 1 in which the distal end portion of the centering wire straightens and is wholly confined within the channel 32.

What is claimed is:

1. In combination,
   an intravascular catheter comprising an elongated tubular body provided with an outer end portion having a tip formed with a discharge orifice, and means for supporting the outer end portion of the catheter within a blood vessel and away from the inner wall lining of said vessel while a treating agent is delivered into the blood vessel through the discharge orifice, said means comprising an elongated flexible wire having in its natural, free state condition, a coiled distal end portion, said catheter having a channel provided with a channel outlet, said wire being received lengthwise within said channel, said wire being slidable in said channel from a retracted position to an operative position in which the distal end portion of said wire projects outwardly from said channel outlet and assumes its natural, coiled condition in contact with the interior wall of the blood vessel to support the outer end portion of said catheter within the blood vessel, and away from the inner lining of the vessel, said wire in said operative position being radially outside the path of flow of the treating agent delivered through said discharge orifice.

2. A combination as defined in claim 1, wherein the distal end portion of said wire, when the wire is in the retracted position thereof, is substantially wholly confined within said channel.

3. A combination as defined in claim 1, wherein said channel defines an elongated, substantially straight passage for the wire.

4. A combination as defined in claim 1, wherein said wire includes an elongated main body portion having a central longitudinal axis and from which the distal end portion extends, the distal end portion, in its natural, free state condition, extending in an arc of at least 3600 about said central longitudinal axis.

5. In combination, an intravascular catheter comprising an elongated tubular body provided with an outer end portion having a tip formed with a central discharge orifice, and means for supporting the outer end portion of the catheter within a blood vessel and away from the inner wall lining of said vessel while a treating agent is delivered into the blood vessel through the discharge orifice, said means comprising an elongated flexible centering wire having in its natural, free state condition, a coiled distal end portion, the outer end portion of said catheter having a side wall formed with an elongated channel extending lengthwise of the outer end portion and having a channel outlet at the tip of said outer end portion, said wire being received lengthwise within said channel, said wire being slidable in said channel from a retracted position in which the distal end portion of said wire is substantially wholly confined within said channel to an operative position in which the distal end portion of said wire projects outwardly from said channel outlet and assumes its natural, coiled condition in contact with the interior wall of the blood vessel to support the outer end portion of said catheter centrally within the blood vessel, and away from the inner lining of the vessel, said wire in said operative position being radially outside the path of flow of the treating agent delivered through said discharge orifice.

6. A combination as defined in claim 5, wherein said wire includes an elongated main body portion having a central longitudinal axis and from which the distal end portion extends, the distal end portion, in its natural, free state condition, extending in an arc of at least 3600 about said central longitudinal axis.

7. A combination as defined in claim 6, wherein said wire is made of spring steel.

8. A combination as defined in claim 6, wherein said wire is made of a resinous thermoplastic material.

* * * * *